(12) United States Patent
Drummond et al.

(10) Patent No.: US 12,343,567 B2
(45) Date of Patent: Jul. 1, 2025

(54) NEUROSTIMULATION USING ENDOLUMINAL FOCUSSED ULTRASOUND

(71) Applicant: The University of Melbourne, Victoria (AU)

(72) Inventors: Jack Drummond, Victoria (AU); Anthony Neville Burkitt, Victoria (AU); David Bruce Grayden, Victoria (AU); Nicholas Lachlan Opie, Victoria (AU); Sam Emmanuel John, Victoria (AU)

(73) Assignee: THE UNIVERSITY OF MELBOURNE, Melbourne (AU)

( * ) Notice: Subject to any disclaimer, the term of this patent is extended or adjusted under 35 U.S.C. 154(b) by 395 days.

(21) Appl. No.: 17/613,425

(22) PCT Filed: May 22, 2020

(86) PCT No.: PCT/AU2020/050511
§ 371 (c)(1),
(2) Date: Nov. 22, 2021

(87) PCT Pub. No.: WO2020/237292
PCT Pub. Date: Dec. 3, 2020

(65) Prior Publication Data
US 2022/0305296 A1    Sep. 29, 2022

(30) Foreign Application Priority Data
May 24, 2019    (AU) .................................. 2019901772

(51) Int. Cl.
*A61N 7/00*    (2006.01)

(52) U.S. Cl.
CPC ........ *A61N 7/00* (2013.01); *A61N 2007/0026* (2013.01); *A61N 2007/0043* (2013.01)

(58) Field of Classification Search
CPC .............. A61N 7/00; A61N 2007/0026; A61N 2007/0043; A61N 7/022;
(Continued)

(56) References Cited

U.S. PATENT DOCUMENTS

| 8,195,272 B2 * | 6/2012 | Piferi | ................. G01R 33/3415 |
| | | | 128/845 |
| 2005/0203366 A1 * | 9/2005 | Donoghue | ........... A61B 5/6814 |
| | | | 607/46 |

(Continued)

FOREIGN PATENT DOCUMENTS

WO    2016/145439 A1    9/2016

OTHER PUBLICATIONS

Search Report for European Patent Application No. 20813053.4 (Jun. 5, 2023).
(Continued)

*Primary Examiner* — Amal Aly Farag
(74) *Attorney, Agent, or Firm* — Merchant & Gould P.C.

(57) ABSTRACT

A neurostimulation device with ultrasound transducer elements is disclosed. The ultrasound transducer elements may be adapted for endoluminal delivery to a deployment site in a lumen of the substrate. The transducer elements may be used to focus acoustic energy, by controlling either the phase delay, time delay, or both, or the ultrasound signals. Further, the plurality of transducer elements may be arranged in a grid arrangement having at least two dimensions.

8 Claims, 8 Drawing Sheets

(58) Field of Classification Search
CPC .... A61N 2007/0078; A61N 2007/0095; A61N 2007/0065; A61B 2018/00321; A61B 2018/00434; A61B 2018/00702
See application file for complete search history.

(56) References Cited

U.S. PATENT DOCUMENTS

| | | | |
|---|---|---|---|
| 2007/0167823 A1* | 7/2007 | Lee | A61B 8/12 600/463 |
| 2008/0312715 A1 | 12/2008 | Asirvatham et al. | |
| 2010/0023088 A1* | 1/2010 | Stack | A61N 1/36114 601/2 |
| 2011/0257523 A1 | 10/2011 | Hastings et al. | |
| 2013/0267853 A1* | 10/2013 | Dausch | A61B 8/4494 600/459 |
| 2014/0058292 A1 | 2/2014 | Alford et al. | |
| 2014/0058294 A1 | 2/2014 | Gross et al. | |
| 2014/0257262 A1 | 9/2014 | Carpentier et al. | |
| 2015/0065922 A1 | 3/2015 | Kohler | |
| 2015/0305716 A1* | 10/2015 | Rice | A61B 8/4461 600/443 |
| 2017/0080255 A1* | 3/2017 | Law | G10K 11/346 |
| 2017/0303840 A1 | 10/2017 | Stadler et al. | |
| 2019/0053781 A1 | 2/2019 | Stigall et al. | |
| 2019/0069949 A1 | 3/2019 | Vrba et al. | |

OTHER PUBLICATIONS

International Search Report and Written Opinion of the International Searching Authority for International Patent Application No. PCT/AU2020/050511 mailed Aug. 3, 2020, 12 pages.

\* cited by examiner

FIG 7

NEUROSTIMULATION USING ENDOLUMINAL FOCUSSED ULTRASOUND

This application is a National Stage Application of PCT/AU2020/050511, filed 22 May 2020, which claims benefit of Serial No. 2019901772, filed 24 May 2019 in Australia, and which applications are incorporated herein by reference. To the extent appropriate, a claim of priority is made to each of the above-disclosed applications.

TECHNICAL FIELD

The present disclosure relates to a device for modulating neural activity using ultrasound energy, and to systems and methods for achieving the same. Specifically but not exclusively, the present disclosure relates to a novel endoluminal ultrasound array device that is deployed in the subject and operable to focus acoustic energy from an array of transducers onto a neuronal stimulation target situated near the device.

BACKGROUND OF INVENTION

Neuromodulation is an effective way to treat a variety of neurological conditions and impairment. For example, Deep Brain Stimulation (DBS) is used clinically for management of drug-resistant Parkinson's disease and epilepsy. It greatly improves the quality of life for affected individuals; in the case of Parkinson's disease, muscle tremors and rigidity are significantly reduced.

DBS systems include one or two leads with electrodes on their end(s) and a pulse generator, all of which are permanently implanted. Burr holes are drilled into the skull and the leads are inserted into the brain through these holes, penetrating several centimetres of brain tissue. The DBS electrodes must be implanted via open brain surgery, which may traumatise the brain, and are sensitive to misalignment. Other risks associated with conventional DBS systems include infection, bleeding from small severed blood vessels, swelling of the brain and disruption of the blood-brain barrier. These risks limit the uptake of treatments like DBS to patients with more advanced disease progression. A study assessing the utility of DBS for earlier stage Parkinson's disease suggests that there is great benefit in implanting the DBS system sooner rather than later. However, until the considerable risks associated with the surgical implantation process for DBS hardware are alleviated, earlier stage DBS is unlikely to be used clinically.

Further complicating the case of conventional DBS, the efficacy of therapy is highly sensitive to the position at which the electrodes are implanted within the brain. A placement error as small as 2.0 mm can be sufficient to result in side effects due to modulation of incorrect brain structure/s and outweigh any therapeutic effect. This may occur due to surgical error or lead migration after implantation. Furthermore, fibrous tissue often forms at the interface between electrodes and the brain over time that may lead to reduced efficacy or device failure. Consequently, DBS is currently reserved for patients in later stages of their disease progression, when the risk to benefit ratio is smaller.

Injecting electric charge into neural tissue is not the only way to modulate its activity. Optical, magnetic, and ultrasonic techniques have been shown to be efficacious and safe under certain conditions.

For example, transcranial focussed ultrasound (tFUS) is a technique used to achieve neural modulation. In this case, an array of ultrasound transducers or a single transducer is placed outside the skull and positioned such that its beam has a maximum intensity at a specified target in the brain. This method suffers from the skull absorbing the majority of the ultrasonic energy and defocussing the beam. This results in a larger volume of tissue surrounding the target being stimulated and, therefore, carries the risk of introducing side effects if applied to achieve DBS.

Intravascular ultrasound (IVUS) catheters, which are deployed endovascularly, provide for imaging and, in some instances, therapy by ablation or heating. These devices contain ultrasound transducers arranged in a 1-dimensional, often circular, array and are removed from the blood vessel after the imaging or therapy has been performed and are not used for neural modulation.

It would be desirable to provide an alternative means to achieve neural stimulation that ameliorates one or more shortcomings of the prior art.

The discussion of the background to the invention included herein including reference to documents, acts, materials, devices, articles and the like is included to explain the context of the present disclosure. This is not to be taken as an admission or a suggestion that any of the material referred to was published, known or part of the common general knowledge in any country as at the priority date of any of the claims.

SUMMARY OF INVENTION

Viewed from a first aspect, the present disclosure provides an endoluminal neurostimulation device including: a plurality of ultrasound transducer elements forming a transducer array; the plurality of transducer elements being provided on or in a substrate layer that is adapted for endoluminal delivery to a deployment site in a lumen of a subject; wherein the transducer elements are operable to focus acoustic energy emitted from the transducer array by controlling one or more of the phase delay and time delay of ultrasound signals emitted from the plurality of transducer elements such that acoustic energy emitted from the transducer array is maximised at a neuronal target near the deployment site to achieve stimulation thereof.

In some embodiments, the transducer array has at least two dimensions.

In some embodiments, the plurality of transducer elements are operable to steer the focussed acoustic energy in a plurality of dimensions, typically three dimensions, by controlling one or more of the phase delay and time delay of ultrasound signals emitted from each of the plurality of transducers.

In some embodiments, the device is configurable to adopt a delivery configuration in which the substrate layer and transducer array are receivable in a delivery lumen for endoluminal delivery to the deployment site, and to adopt deployed configuration in which the substrate layer is arranged with the transducer elements coupled, directly or indirectly with the luminal wall once deployed from the delivery lumen.

In some embodiments, the substrate layer has elastic properties such that it is able to be stretched longitudinally to adopt the delivery configuration and reshapes when deployed from the delivery lumen to adopt the deployed configuration when in situ. The substrate layer may be collapsible or compressible to adopt the delivery configuration and expandable when deployed from the delivery lumen to adopt the deployed configuration when in situ.

In some embodiments, the substrate layer and the transducer array have a substantially tubular overall shape when deployed in the lumen of the subject.

In some embodiments, the plurality of transducer elements are arranged on or in the substrate layer to direct ultrasound signals only towards the neuronal target.

In some embodiments, the substrate layer is flexible to accommodate contours within the lumen of the subject in which the device is deployed.

In some embodiments, the acoustic energy emitted from the plurality of transducer elements is in the range of 0.5 MHz to 60 MHz, preferably 0.5 MHz to 30 MHz, more preferably 0.5 MHz to 20 MHz and more preferably still 0.5 MHz to 5 MHz.

In some embodiments, the device includes a control circuit for controlling operation of the plurality of transducer elements to achieve one or both of focus and steering of the acoustic energy emitted from the transducer array. The control circuit may be configurable to disable transducer elements in the transducer array that are not required to achieve therapeutic neurostimulation.

In some embodiments, the control circuit controls one or both of the amplitude and the frequency of the ultrasound signals emitted by each of the transducer elements in the transducer array.

In some embodiments, the control circuit is configurable to focus and/or steer the ultrasound signals emitted from the transducer elements so that the acoustic energy emitted from the transducer array is maximised at a plurality of neuronal targets.

In some embodiments, the control circuit resides on or in one or both of the substrate and a backing layer of the transducer array.

In some embodiments, the control circuit is provided in a hermetically sealed housing that is configured for subcutaneous implantation in the subject and operatively coupled with the transducer array by one or more wires.

In some embodiments, the device is configured for long term placement in a vascular lumen of the subject, for therapeutic neuromodulation by stimulation of the neuronal target for the treatment of one or more chronic conditions selected from a group including but not limited to Parkinson's disease, epilepsy, obsessive compulsive disorder and addiction.

In some embodiments, the device is configured for long term placement in the Basal vein of Rosenthal (BVR) for therapeutic neuromodulation by stimulation of one or both of the internal globus pallidus (GPi) and the subthalamic nucleus (STN) for the treatment of Parkinson's disease.

Viewed from a second aspect, the present disclosure provides a neurostimulation system comprising: an endoluminal neurostimulation device having a plurality of ultrasound transducer elements forming a transducer array, the plurality of transducer elements being provided on or in a substrate layer that is adapted for endoluminal delivery to a deployment site in a lumen of a subject; a programmable control circuit for controlling operation of the plurality of transducer elements to achieve one or both of focus and steering of acoustic energy emitted from the transducer array; and a power source for supplying power to the control circuit and the plurality of transducer elements; wherein the control circuit is programmable to control one or both of the phase and time delay of ultrasound signals emitted from each of the plurality of transducer elements such that acoustic energy emitted from the transducer array is maximised at a neuronal target near the deployment site to achieve stimulation thereof.

In some embodiments, the transducer array has at least 2 dimensions;

In some embodiments, the power source is implantable, and the system includes a charging coupling for charging the power source once implanted.

In some embodiments, the endoluminal neurostimulation device is configurable to adopt a delivery configuration in which the substrate layer and transducer array are receivable in a delivery lumen for endoluminal delivery to the deployment site, and to adopt a deployed configuration in which the substrate layer is arranged with the transducer elements coupled directly or indirectly with the luminal wall once deployed from the delivery lumen.

In some embodiments, the substrate layer and the transducer array have a substantially tubular overall shape when deployed in the lumen of the subject.

In some embodiments, the control circuit is programmable to achieve one or more of: disabling transducer elements directed away from the neuronal stimulation target when in situ; controlling the amplitude of ultrasound signals emitted by each of the transducer elements; controlling the frequency of ultrasound signals emitted by each of the transducer elements; and focus and/or steering of the ultrasound signals emitted from the transducer elements so that the acoustic energy emitted from the transducer array converges on a plurality of neuronal targets.

In some embodiments, the control circuit resides on or in one or both of the substrate layer and a backing layer of the transducer array.

In some embodiments, the control circuit is provided in a hermetically sealed housing that is configured for subcutaneous implantation in the subject and operatively coupled with the transducer array by one or more wires. The hermetically sealed housing may also contain a power source.

In some embodiments, the control circuit is programmable using a device external to the subject that is operatively couplable with the control circuit.

Viewed from a third aspect, the present disclosure provides a kit for the provision of endoluminal neurostimulation therapy in a subject, the kit including: an implantable endoluminal neurostimulation device having a plurality of ultrasound transducer elements forming a transducer array, the plurality of transducer elements being provided on or in a substrate layer that is adapted for endoluminal delivery to a deployment site in a lumen of a subject; a control circuit for controlling operation of the plurality of transducer elements to achieve one or both of focus and steering in a plurality of dimensions of acoustic energy emitted from the transducer array, a power source for supplying power to the controller and the plurality of transducer elements; a delivery lumen containing the endoluminal neurostimulation device in a delivery configuration; and a guide wire; wherein the control circuit is operable to control one or more of the phase delay and time delay of ultrasound signals emitted from individual ones of the plurality of transducer elements such that acoustic energy emitted from the transducer array is maximised at a neuronal target near the deployment site to achieve stimulation thereof.

In some embodiments, the delivery lumen is an endovascular delivery catheter. The endovascular delivery catheter may be configured for delivery of the endoluminal neurostimulation device to brain vasculature for long term placement to achieve therapeutic neuromodulation by stimulation of the neuronal target for ongoing treatment of one or more neurological conditions.

Other aspects of the disclosure include methods for neural stimulation using the endoluminal neurostimulation device according to the first aspect or the neurostimulation system of the second aspect of the invention.

It is to be understood that features described in the context of one aspect of the disclosure have corresponding applicability in other aspects of the disclosure even when not explicitly stated.

BRIEF DESCRIPTION OF DRAWINGS

The present invention will now be described in greater detail with reference to the accompanying drawings. It is to be understood that the embodiments shown are examples only and are not to be taken as limiting the scope of the invention as defined in the claims appended hereto.

DETAILED DESCRIPTION

Figure 1A:
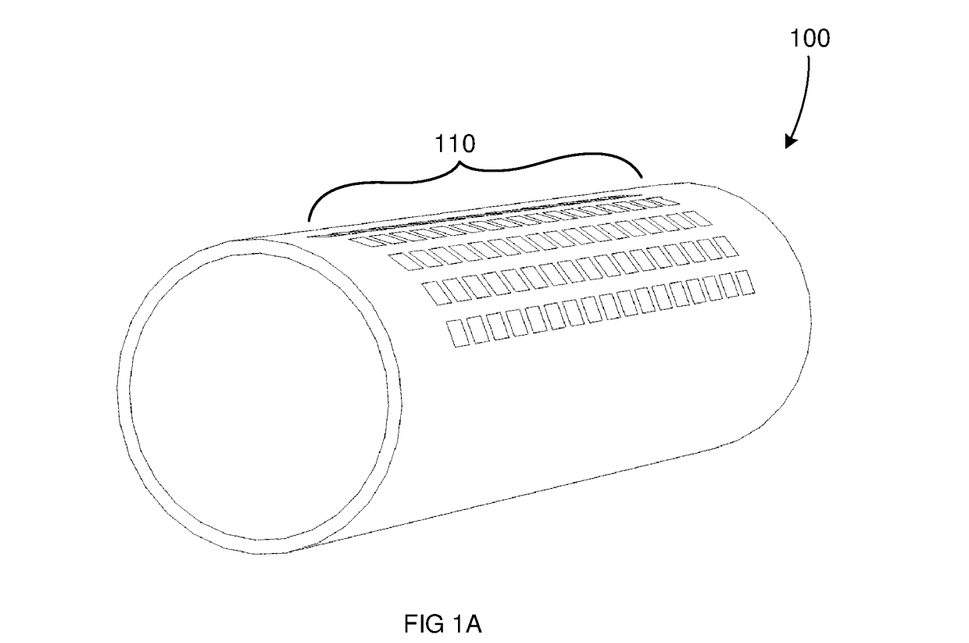
FIG. 1A is an isometric schematic view representing an endoluminal neurostimulation device in a deployed configuration according to one embodiment.
Figure 1B:
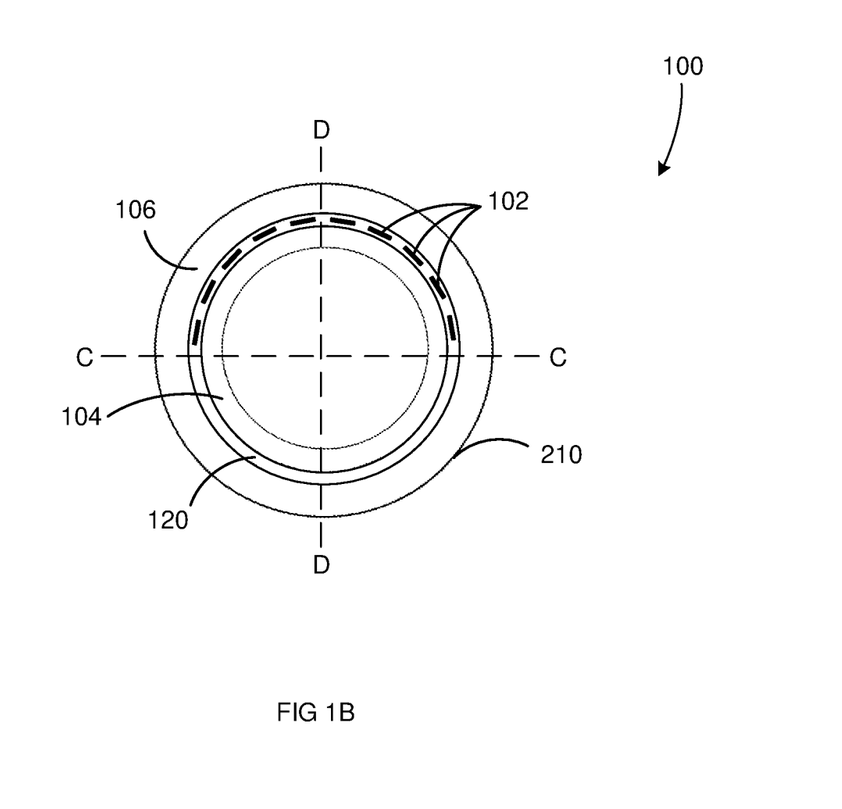
FIG. 1B (not to scale) is an end view of the device of FIG. 1A.
Figure 1C:
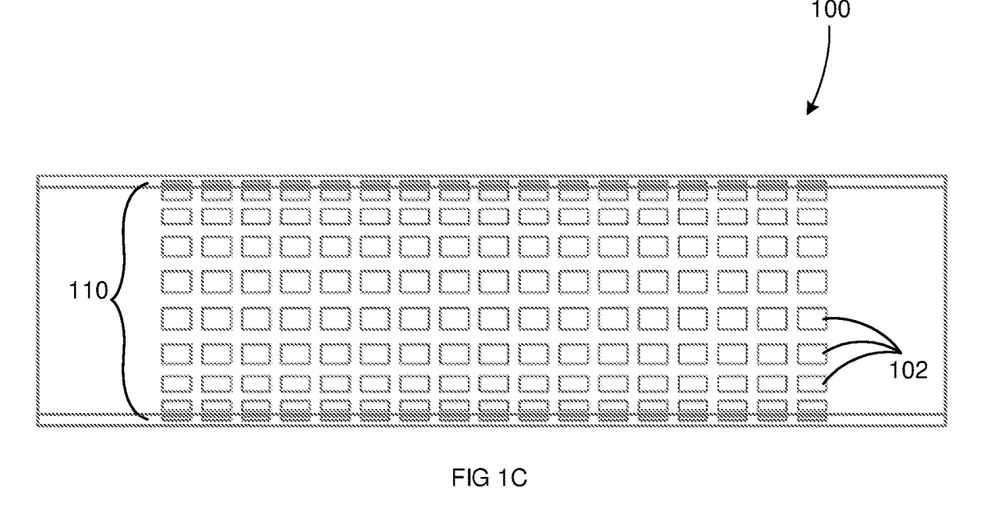
FIGS. 1C and 1D are cross sectional views of the device in FIG. 1B taken through the lines C-C and D-D respectively.
Figure 1D:
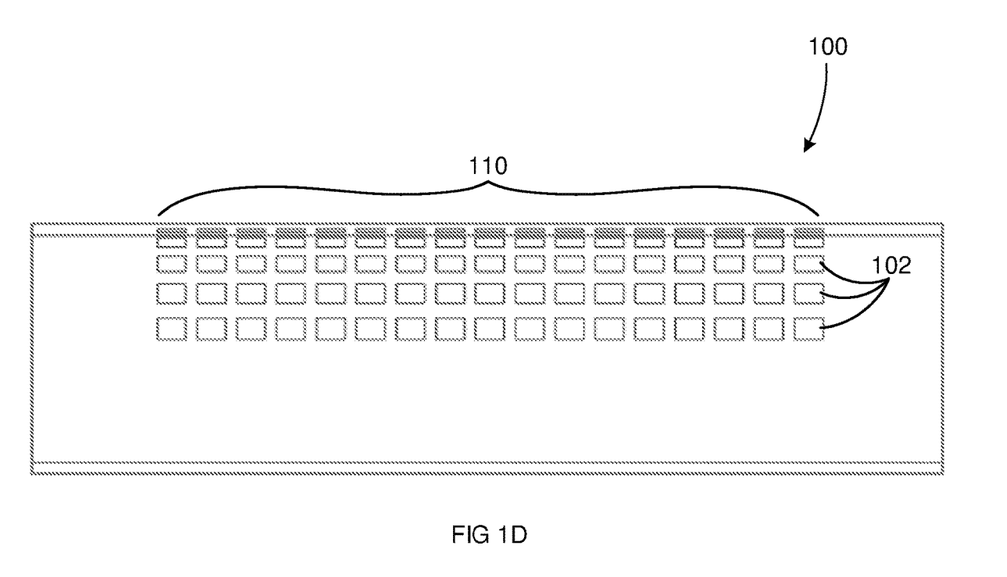

Referring firstly to FIGS. 1A to 1D, there is shown an endoluminal neurostimulation device 100 according to an embodiment of the disclosure. FIG. 1A is an isometric view and FIGS. 1C and 1D are cross sectional views of the device in FIG. 1B taken through the lines C-C and D-D respectively. FIG. 1B is an end view showing various layers of the device as may be incorporated in some embodiments.

The device includes a plurality of ultrasound transducer elements 102 forming a transducer array 110. Ideally, the transducer array 110 has at least two dimensions to achieve focus in multiple dimensions. The plurality of transducer elements 102 are provided on or in a substrate layer 120 that is adapted for endoluminal delivery to a deployment site in a lumen of a subject. The lumen may be any lumen within the subject's body that is accessed non-surgically (e.g. lumens of the respiratory, renal or digestive systems), or using minimally invasive surgical techniques (e.g. lumens of the reproductive system or the vasculature). In preferred embodiments, the endoluminal neurostimulation device 100 is an endovascular device although the scope of the disclosure is not limited to this application.

The plurality of transducer elements 102 are operable to focus acoustic energy emitted from the transducer array 110 by controlling the ultrasound signals they each emit. In the case of continuous ultrasound signals, focussing is achieved by controlling the phase delay of the signals emitted by each of the transducer elements 102. In the case of pulsed ultrasound signals, focus is typically achieved by applying a time delay to the signals emitted by each of the transducer elements 102 although a phase delay may also be applied. It is to be understood that the phase delay may be positive or negative, in the sense that it may be a phase shift in either the positive or the negative direction. Similarly, the time delay may be positive or negative in the sense that it may be a delay or advancement of the waveform. In any case, the phase/time delay applied to ultrasound signals emitted from each of the plurality of transducer elements 102 is such that acoustic energy emitted from the transducer array 110 is maximised at a neuronal target near the deployment site to achieve stimulation thereof. It is to be understood that the neuronal target may be a point target, an elongate target, a target area or volume or a target pattern aimed at one or more neurons or neuronal tissue. Acoustic energy may also be referred to as acoustic intensity, being the power delivered per unit of area cross sectional to the acoustic beam path.

Figure 2:
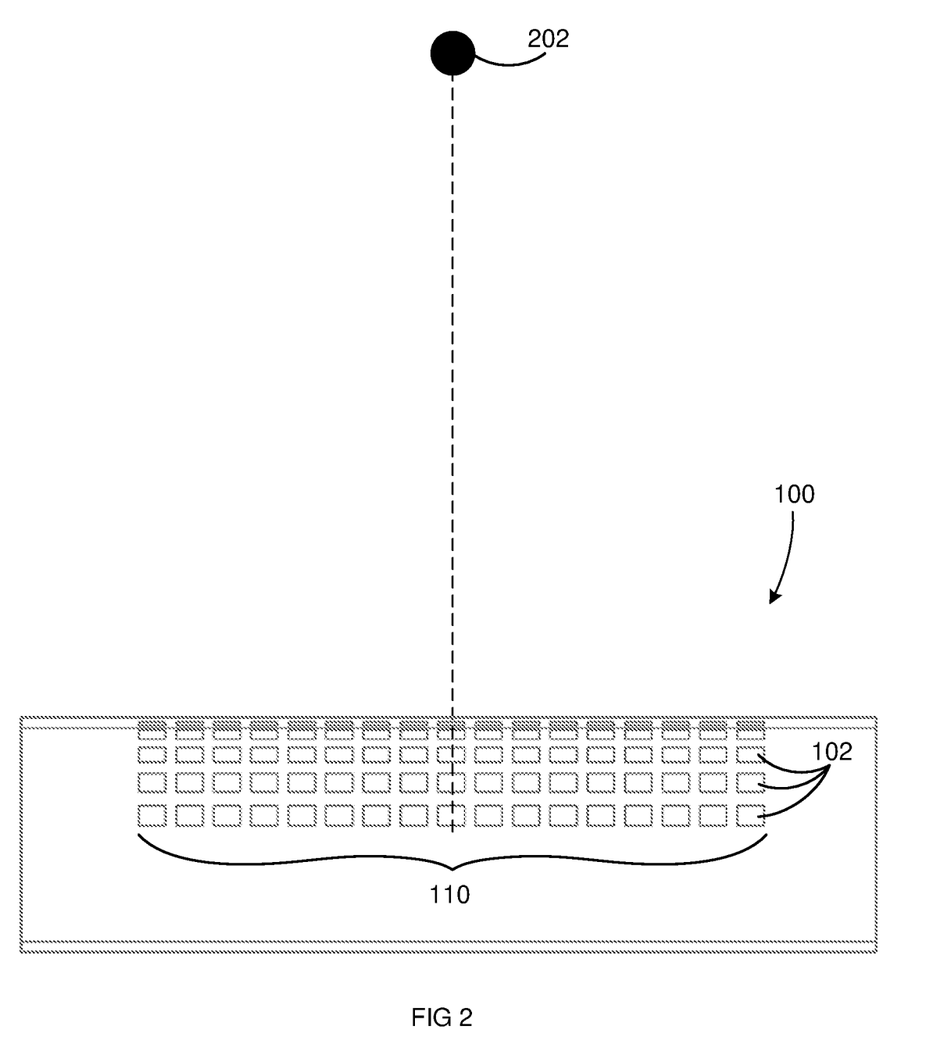
FIG. 2 is schematic drawing illustrating a neuronal target to which acoustic energy of an endoluminal neurostimulation device is focussed.

FIG. 2 is a schematic drawing illustrating a neuronal target 202 to which acoustic energy of an endoluminal neurostimulation device is focussed according to an embodiment of the disclosure.

The arrangement and operation of the ultrasound transducer array 110 according to embodiments of the present disclosure may be referred to as a phased array comprised of N transducers centred at $r_i$, where i=1,2, ..., N-1, N. In the case of pulsed ultrasound, to bring the ultrasound signals emitted by the N transducers to a focus at a focal point $r_t$ in the tissue, the delay applied to the pulse emitted by the $i^{th}$ transducer may be guided according to Equation 1, where $r_i$ and $r_t$ are position vectors, and c is the speed of sound in the tissue.

$$\delta t_i = c|r_f - r_i| \quad \text{(Equation 1)}$$

In the case of continuous ultrasound, to bring the ultrasound signals emitted by the N transducers to a focus at a focal point $r_f$ in the tissue, the delay applied to the phase of the ultrasound wave emitted by the $i^{th}$ transducer may be guided according to Equation 2, where $\lambda$ is the ultrasound wavelength.

$$\delta\theta_i = \frac{2\pi}{\lambda}|r_f - r_i| \quad \text{(Equation 2)}$$

It is to be understood however that due to differences between the geometric focus and the acoustic focus of the transducer array, Equations 1 and 2 typically provide a starting point for determining the required time or phase delay, and an adjustment may be required to compensate for discrepancies between these foci. Such discrepancies are larger for arrays of smaller dimensions and may, for example, result in an acoustic focus closer to the array than intended, if not accounted for. Since the plurality of transducer elements 102 may be operated to focus the ultrasound energy in three dimensions by controlling the time delay and/or phase delay of the emitted ultrasound signals of each transducer element, the acoustic energy emitted from the transducer array 110 may be steered in three dimensions, in addition to being focussed.

Figure 3:
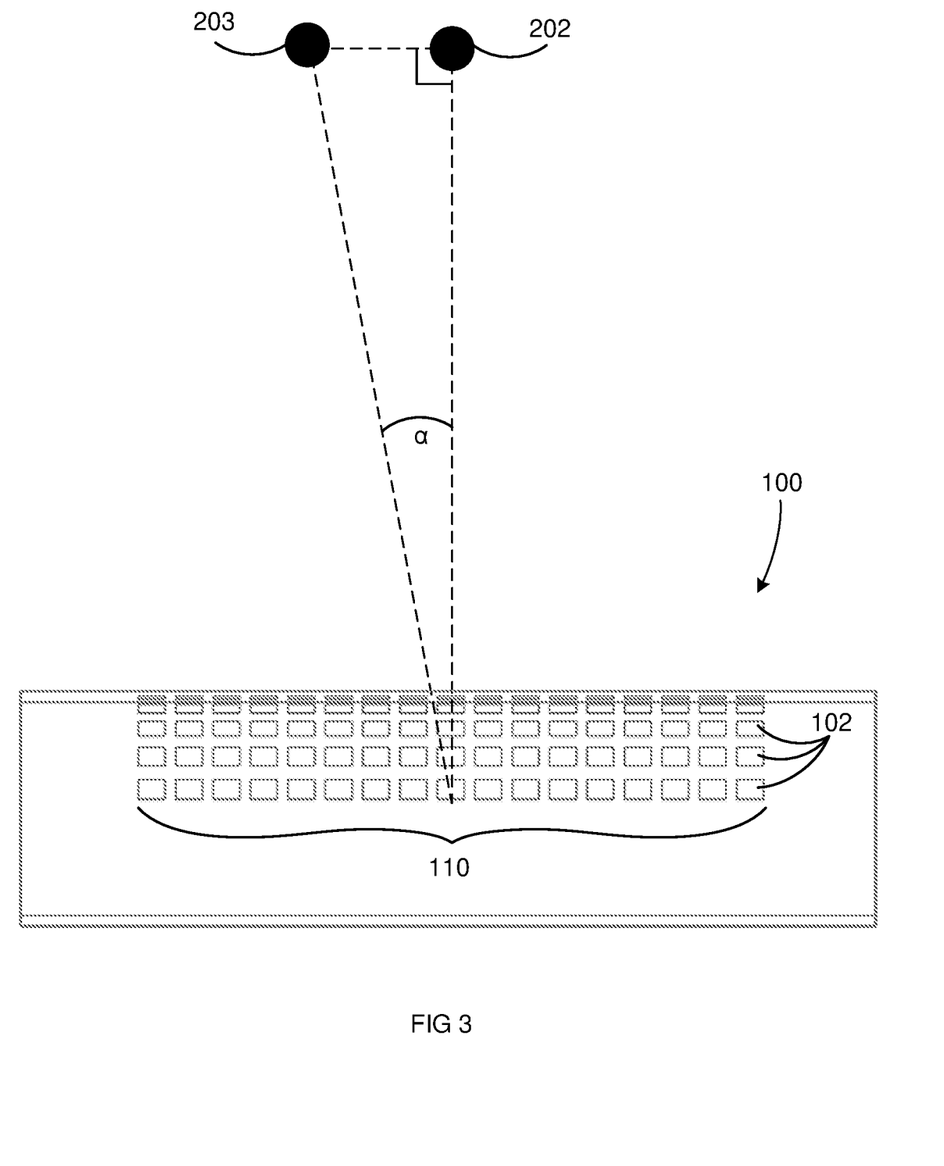
FIG. 3 is a schematic drawing illustrating a neuronal target to which acoustic energy of an endoluminal neurostimulation device is steered along a longitudinal dimension of the transducer array.

FIG. 3 is a schematic drawing illustrating a neuronal target 203 to which acoustic energy emitted from the transducer array of an endoluminal neurostimulation device is both focussed and steered according to an embodiment of the disclosure. Acoustic energy emitted from the transducer array 110 when in situ may be deposited into the tissue at an angle α and this may be varied by altering the delay/phase shift applicable to the transducer elements 102. Since the acoustic energy emitted from the transducer array 110 is steerable, the inventive endoluminal device is less sensitive to placement errors than electrodes implanted directly into the target since the "beam" of acoustic energy emitted from the transducer array 110 may be steered onto the neuronal target to compensate for non-optimum placement of the device.

The phase/time delay and frequency of each transducer element may be varied from time to time during long term use of the device e.g. to re-focus the acoustic energy emitted from the transducer array as the subject's disease state changes or if the device migrates within the lumen. Additionally/alternatively, the phase/time delay and frequency of each transducer element may be varied dynamically, i.e. changed in a more acute setting to produce a continuously varying focal point over a shorter period of time. For example, it is possible to focus the emitted energy so that it is maximised at a focal point that shifts or oscillates along the length of the array or along, around or within a neuronal target that is not a single fixed point.

FIG. 1B shows layers of an endoluminal neurostimulation device 100 according to an embodiment of the disclosure. Here, substrate layer 120 has a mesh or web-like structure into which the transducer elements 102 are fabricated, deposited or embedded. However, in alternative embodiments, substrate layer 120 may provide a surface onto which transducer elements 102 are deposited or mounted. The transducers may be capacitive micromachined ultrasound transducers (CMUTs) or any small-scale transducer such as piezoelectric micromachined ultrasound transducers (PMUTs) and conventional piezoelectric ultrasound transducers, most commonly made from PZT (lead zirconate titanate). Typically, the transducer elements 102 are 25 µm-300 µm in size. It is to be noted that a transducer element may be composed of multiple smaller transducer cells whose outputs are identical.

The substrate layer 120 surface may be continuous, woven, smooth, undulating, a web, mesh, scaffold or other structure that enables or enhances adoption of a delivery configuration in which the cross-sectional dimension of the device is reduced and the substrate layer and transducer array 110 are receivable in a delivery lumen (not shown) for endoluminal delivery to the deployment site.

In some embodiments, the substrate layer 120 is flexible to accommodate the curvature of the vasculature or other body lumen into which the device is deployed. In some embodiments, substrate layer 120 and transducer array 110 may be collapsible or may be rolled upon itself, allowing the device to fit inside a delivery lumen for delivery to the deployment site. In preferred embodiments, the substrate layer 120 and transducer array 110 adopt a deployment configuration in which they are deliverable in an endovascular catheter by catheter angiography or the like to a deployment site.

It is to be understood that although the device in many applications is intended for permanent or long term deployment in a lumen, it is contemplated that the device may be removed and/or relocated after initial deployment.

In preferred embodiments, substrate layer 120 has a maximum thickness of about 15 to 20 µm to assist with formation of the delivery configuration in relatively small diameter body lumens of the subject, including the brain vasculature which may have an endoluminal diameter of less than 2 mm. In some preferred embodiments, substrate layer 120 has elastic properties such that it is able to be stretched longitudinally (and/or contracted laterally) to adopt the delivery configuration and reshapes when deployed from the delivery lumen to adopt the deployed configuration when in situ. Ideally, the substrate layer material conforms to the endoluminal wall shape when deployed. Suitable materials may include polydimethylsiloxane (PDMS) which is amenable to fabrication of the substrate layer 120 using various methods including e.g. a trench refilling technique. Using this technique, transducer elements 102 are fabricated onto a silicon or other substantially rigid substrate base, trenches or voids are etched into the substrate base between the transducer elements, the trenches or voids are filled (e.g. with PDMS or other flexible substrate layer material) and the substrate base is removed. The result is individual transducer elements 102 linked by a thin substrate layer 120 between them which improves flexibility.

The transducer elements 102 may be acoustically coupled with the vascular wall directly or indirectly. The embodiment shown in FIG. 1B provides an impedance matching layer 106 which is arranged between the substrate layer 120 containing transducer elements 102 and the endoluminal wall 210 to help to minimise the mismatch between the acoustic impedance of the substrate layer 120 and the surrounding tissue thereby maximising the acoustic energy deposited into the tissue. The thickness of the impedance matching layer 106 is ideally one quarter of the ultrasound wavelength λ. Matching layer 106 may be formed by a single continuous material layer over transducer array 110, or by a plurality of matching layer segments formed over individual ones or groups of transducer elements 102 in transducer array 110 to reduce the bulk of the device and particularly, the cross sectional thickness of the device while in the delivery configuration. Ideally, the impedance $Z_m$ of the matching layer 106 is determined according to Equation 3 where $Z_t$ is the impedance of the transducer elements and $Z_e$ is the impedance of the endoluminal wall.

$$Z_m = \sqrt{Z_t \cdot Z_e} \quad \text{(Equation 3)}$$

Also shown in FIG. 1B is backing layer 104 which may be included to absorb or dampen ultrasound waves propagating toward the centre of the lumen by providing high acoustic impedance relative to the tissue. Additionally, backing layer 104 may assist in providing a firm coupling between the transducer elements 102 or matching layer 106 and the endoluminal wall 210 whilst also being flexible enough to accommodate the delivery configuration and the curvature of the body lumen into which the device is deployed. When provided, backing layer 104 need only cover part(s) of the substrate layer 120 on or in which there are transducer elements 102 although for ease of manufacture, backing layer 104 may cover substantially all of the substrate layer 120. It is to be understood that each of the impedance matching layer 106 and the backing layer 104 possess properties that enable the device, when incorporating these layers, to adopt a delivery configuration in which the cross-sectional thickness of the device 100 is reduced so that it is receivable in a delivery lumen for endoluminal delivery to the deployment site.

In the embodiment represented in FIGS. 1A to 1D, transducer elements 102 are in a grid arrangement in substrate layer 120 which has a tube-like shape when in the deployed configuration. Transducer elements 102 cover approximately half of the substrate layer 120 since transducer elements provided on the opposing side of the tube to the neuronal target are redundant. However, until deployment techniques are developed which ensure that the device 100 is deployed within the body lumen with the transducer array 110 oriented toward the neuronal target, it may be desirable to arrange a larger number of transducer elements 102 in an array 110 on or in substantially the entire area of the substrate layer 120, and to deactivate transducer elements that are not required to achieve stimulation of the neuronal target.

Preferably, the transducer elements 102 are spaced with a pitch of less than half the ultrasound wavelength λ they emit, where the pitch is the distance between the centres of adjacent transducer elements. This mitigates formation of side lobes in the beam of acoustic energy emitted from the transducer array 110 which, when present, may cause undesirable effects such as stimulation of non-target neurons and side-effects for the subject.

While the substrate layer 120 in FIG. 1B provides a closed tube having an annular cross section, it is to be understood that this need not be the case and the substrate may alternatively form an open seam tube or a partial-round tube or other shape when deployed in the body lumen. In some embodiments, the substrate layer 110 and the transducer array 120 are configured to adopt the shape and/or contour of the endoluminal deployment site. It is to be understood that whatever the shape and configuration of the device, fluid may flow through or past the device when in situ.

Typically, the acoustic energy emitted from the plurality of transducer elements 102 is in the range of 0.5 MHz to 5 MHz. Frequencies utilised at the higher end of the range are able to achieve tighter focus of the ultrasound signals emitted from each of the transducer elements 102 and so may be safer in the clinical environment, avoiding excitation of neurons and other tissue that are outside the target area. In some embodiments, frequencies of up to 60 MHz may be contemplated, particularly in the case of pulsed ultrasound since a pulsing strategy incorporating cooling periods may be adopted to mitigate heating issues that might otherwise develop.

In preferred embodiments, the endoluminal neurostimulation device 100 includes a control circuit (not shown) for controlling operation of the plurality of transducer elements 102 to achieve one or both of focus and steering of the acoustic energy emitted from the transducer array 110. In embodiments where the substrate layer 120 includes transducer elements 102 that are oriented away from the neuronal target 202/203, the control circuit may be programmable to disable those transducer elements. In some embodiments, the control circuit is programmable to control individually the amplitude of acoustic signals emitted from one or more of the plurality of transducer elements 102. Shaping the signal amplitude in this way may be useful in steering and focussing the acoustic energy emitted from the transducer array 110. Alternatively/additionally, the control circuit may be programmable to control the frequency at which one or more of the transducer elements 102 (or groups thereof) transmit ultrasound energy which may be desirable if the location of the neuronal target may vary during use of the device or where the position of the neuronal target shifts or oscillates.

In some embodiments, the control circuit is configurable to focus and/or steer the ultrasound signals emitted from the transducer elements 102 so that the acoustic energy emitted from the transducer array 110 converges on a plurality of neuronal targets. Multiple targets may be stimulated simultaneously, or sequentially in a multiplexed control strategy.

In some embodiments, the control circuit is an application-specific integrated circuit (ASIC) that resides on or in the substrate layer 120, or on or in the backing layer 104. However, it is to be understood that the transducer elements 102 may alternatively be driven by a control circuit provided at a different location and in operative communication with the array of transducer elements. In one example, the control circuit is provided in a hermetically sealed housing that is configured for subcutaneous implantation in the subject and is operatively coupled with the transducer array by one or more wires running through the body lumen. Typically, the control circuit housing is implanted subcutaneously in the torso but alternative locations include the neck, arm, leg and the like so as to provide relatively easy access for replacement if necessary.

Preferably, the control circuit is programmable using a device external to the subject that is operatively couplable with the control circuit ideally using a wireless communication interface.

In some applications, the device is configured for long term placement in a vascular lumen of the subject, for therapeutic neuromodulation by stimulation of the neuronal target for the treatment of one or more chronic conditions such as but not limited to Parkinson's disease, epilepsy, obsessive compulsive disorder and addiction to name a few.

An endoluminal neurostimulation device according to embodiments of the disclosure may be configured for long term placement in the in the basal vein of Rosenthal (BVR) for therapeutic neuromodulation by stimulation of the internal globus pallidus (GPi) or subthalamic nucleus (STN) for the treatment of Parkinson's disease.

A neurostimulation system according to another aspect of the disclosure comprises an endoluminal neurostimulation device having a plurality of ultrasound transducer elements forming a transducer array. The plurality of transducer elements are provided on or in a substrate layer that is adapted for endoluminal delivery to a deployment site in a lumen of a subject. A programmable control circuit controls operation of the plurality of transducer elements to achieve one or both of focus and steering of acoustic energy emitted from the transducer array. A power source supplies power to the control circuit and the plurality of transducer elements. The control circuit is programmable to control the phase and/or time delay of ultrasound signals emitted from each of the plurality of transducer elements such that acoustic energy emitted from the transducer array is maximised at a neuronal target near the deployment site to achieve stimulation thereof. Typically, the array is a two dimensional array.

As described in the context of the device of FIGS. 1A to 1D, the device of the system is configurable to adopt a delivery configuration in which the substrate layer and transducer array are receivable in a delivery lumen for endoluminal delivery to the deployment site, and to adopt a deployed configuration in which the substrate is arranged with the transducer elements in contact with the endoluminal wall once deployed from the delivery lumen.

As described in the context of the device of FIGS. 1A to 1D, the substrate layer 110 and the transducer array 120 preferably have a substantially tubular overall shape when deployed in the lumen of the subject. However it is to be understood that the substrate layer 110 and the transducer array 120 are ideally configured to adopt the shape and/or contour of the endoluminal deployment site. The substrate layer 110 may be stretched, rolled, compressed or otherwise reduced so that the cross-sectional dimension of the device 100 is reduced for being received in a delivery lumen for endoluminal delivery to the deployment site. Additional layers such as an impedance matching layer and a backing layer may be provided in some embodiments.

In preferred embodiments, the control circuit is programmable to achieve one or more of: disabling transducer elements directed away from the neuronal stimulation target when in situ; controlling the amplitude of ultrasound signals emitted by each of the transducer elements; controlling the frequency of ultrasound signals emitted by each of the transducer elements. Alternatively/additionally the control circuit may be programmable to operate individual ones of the plurality of transducer elements to focus and/or steer acoustic energy at a plurality of neuronal targets. Multiple targets may be stimulated simultaneously, or sequentially in a multiplexed control strategy. In some embodiments, the control circuit resides on or in the substrate or backing layer although this need not be the case and the control circuit may be e.g. provided in a hermetically sealed housing that is configured for subcutaneous implantation elsewhere in the subject and operatively coupled with the transducer array by one or more wires. In this arrangement the hermetically sealed housing may also contain the power source and the charging coupling is ideally a contactless coupling using electromagnetic charge transfer or the like to charge the power source.

The control circuit may be programmable using a device external to the subject that is operatively couplable with the control circuit ideally using a wireless communication interface. The programming device may be e.g. a handheld device, desktop or mobile computer or bespoke device configured to program the control circuit to operate the plurality of transducer elements 102 according to a stimulation strategy developed by a clinician, typically in conjunction with software that takes into account parameters such as those outlined in Table 1.

TABLE 1

| Category | Symbol | Description | Value |
| --- | --- | --- | --- |
| Ultrasound | c | Speed of sound | 1552.5 m/s |
| | f | Frequency | 2.0 MHz |
| | λ | Wavelength | 776.25 μm |
| Focal Point | $F_R$ | Radial component of focal point | 6.1 mm |
| | $F_\Phi$ | Angular component of focal point | 0.0° |
| | $F_z$ | Longitudinal component of focal point | 0.0 mm |
| Array Dimensions | $R_v$ | Radius | 1.0 mm |
| | $L_\Phi$ | Angular extent | 160° |
| | $L_z$ | Longitudinal extent (length) | 6.0 mm |
| Transducer Dimensions | $\Delta_z$ | Length of transducers | 250 μm |
| | $\delta_z$ | Longitudinal pitch of transducers | 350 μm |
| | $N_z$ | Number of transducers along | 17 |

TABLE 1-continued

| Category | Symbol | Description | Value |
| --- | --- | --- | --- |
| | | array | |
| | $\Delta\Phi$ | Angular width of transducers | 10.0° (191.0 μm) |
| | $\delta\Phi$ | Angular pitch of transducers | 17.8° (336.2 μm) |
| | $N_\Phi$ | Number of transducers around array | 10 |

A kit according to another aspect of the disclosure, for the provision of endoluminal neurostimulation therapy in a subject, includes an implantable endoluminal neurostimulation device having a plurality of ultrasound transducer elements forming a transducer array, the plurality of transducer elements being provided on or in a substrate layer that is adapted for endoluminal delivery to a deployment site in a lumen of a subject. A programmable control circuit controls operation of the plurality of transducer elements to achieve one or both of focus and steering of acoustic energy emitted from the transducer array. A power source supplies power to the controller and the plurality of transducer elements. A guide wire and a delivery lumen containing the endoluminal neurostimulation device in a delivery configuration are also supplied in the kit. As described in the context of embodiments of the endoluminal neurostimulation device and the neurostimulation system, the control circuit is programmable to control the phase delay and/or time delay of ultrasound signals emitted from each of the plurality of transducer elements such that acoustic energy emitted from the transducer array is maximised at a neuronal target near the deployment site to achieve stimulation thereof.

Typically, the delivery lumen is an endovascular delivery catheter although delivery catheters suitable to deliver the device to non-vascular lumens of the subject's body such as in the respiratory, digestive, renal and reproductive systems are also contemplated and within the scope of this disclosure.

In some embodiments, the kit contains an endovascular delivery catheter configured for delivery of the endoluminal neurostimulation device to the brain vasculature, such as the BVR or anterior septal veins (ASV), for long term placement of the device to achieve therapeutic neuromodulation by stimulation of a neuronal target such as the GPi or STN for ongoing treatment of one or more neurological conditions such as, for example, Parkinson's disease.

The GPi and STN have been identified as neuronal targets in close proximity to the BVR in the brain into which the inventive device may be deployed. In a sample of subjects, both targets were on average less than 10 mm from the BVR whose diameter was typically in the range of 1 to 5 mm with a mean of 2 mm. The STN and GPi had a mean separation of 6.1 mm and 8.5 mm respectively from the BVR making them both potential targets for stimulation using embodiments of the present disclosure. Assuming the diameter of the BVR is its mean value, the focal lengths (distance from centre of array surface to neuronal target) of a transducer array according to an embodiment of the present disclosure, deployed optimally within the BVR to target the GPi and STN are 5.1 mm and 7.5 mm respectively.

The GPi may be regarded as a more feasible neuronal target due to its closer proximity to the BVR and the straightness of the BVR as it passes the GPi. This suggests that DBS utilising embodiments of the present disclosure may be feasible by endovascularly deploying the device into the BVR by catheter angiography or other minimally invasive techniques, for stimulation of the GPi on an ongoing basis to achieve neuromodulation in the treatment of e.g. Parkinson's disease.

Example 1

The GPi is a deep brain stimulation (DBS) target for Parkinson's disease. A simulation of neural stimulation of the GPi from a device 100 deployed in the BVR was executed in k-Wave, a freely available software library that works with MATLAB, using the parameters in Table 1. The radius of the transducer array 110 was chosen to be 1.0 mm to match the mean radius of the BVR. The acoustic energy emitted from the transducer array 110 was focussed to 6.1 mm from the centre of the BVR (see FIG. 2) to reflect the minimum separation between the BVR and the GPi. This value of 6.1 mm is an estimate of the mean across 152 humans (unpublished data) although this value may vary from subject to subject and between subject cohorts. Although the BVR is curved, the simulation was simplified by modelling the device 100 as being straight.

An ultrasound frequency of 2.0 MHz was chosen so that approximately one full acoustic pressure phase cycle would be present around the angular extent of the array facing the target when used as a phased array to focus the acoustic energy emitted from the transducer array. Based on this choice of frequency, an array length of 6.0 mm was chosen so that approximately one full acoustic pressure phase cycle would be present along the longitudinal extent of the array when used as a phased array to focus the beam. Ideally, at least one full acoustic pressure phase cycle should be present around and along the transducer array to produce concave wavefronts which converge to a focus at the neuronal target. The more pressure phase cycles on the array surface, the less the spread of acoustic intensity (and hence neural stimulation) about the neuronal target and thus the greater the spatial precision (desired).

A phase delay $\delta\theta_i$ was applied to each transducer element 102 proportional to the distance between its centre position $r_i$ and the neuronal target position $r_t$ guided by Equation 2.

The ultrasound transducers were arranged with a pitch (distance between centre of adjacent ultrasound transducers) less than half the ultrasound wavelength to avoid side-lobe formation. In this case, the ultrasound wavelength is 776 µm.

Figure 4A:
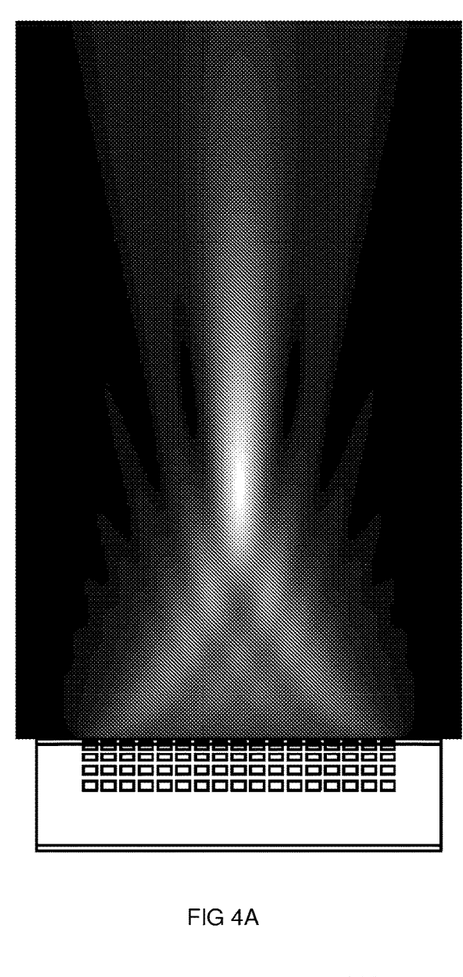
FIGS. 4A and 4B are normalised intensity plots for a simulated endoluminal neurostimulation device deployed in a brain model, viewed from the side of the device as represented in FIG. 1D and the end of the device as represented in FIG. 1B, respectively.
Figure 4B:
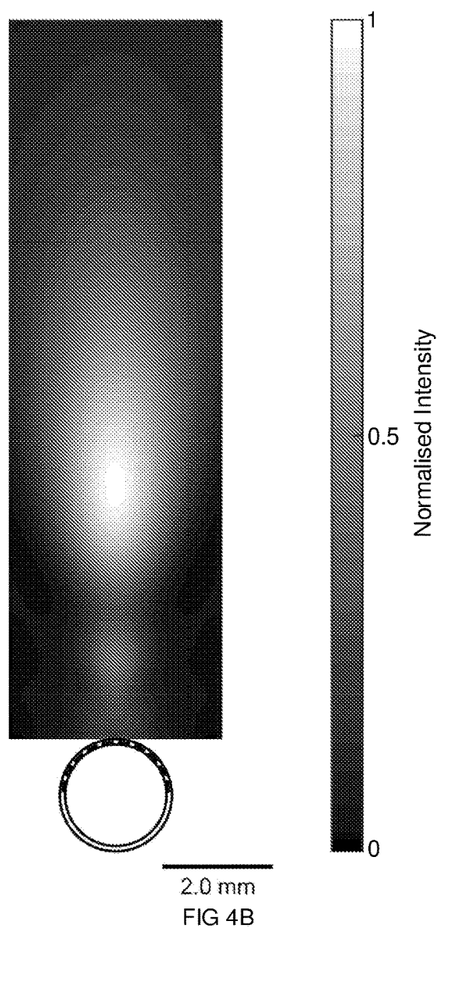

Only transducers facing toward the neuronal target were included in the simulation. FIGS. 4A and 4B are normalised intensity plots for a simulated endoluminal neurostimulation device according to an embodiment of the disclosure deployed endovascularly in a brain model, as viewed from the side of the device in FIG. 1D and the end of the device in FIG. 1B, respectively. FIGS. 4A and 4B show that for the simulated device, the ultrasound signals emitted from the transducer elements 102 are focussed such that the acoustic energy emitted by the transducer array 110 is maximised at neuronal target 202 as represented in FIG. 2.

Figure 4C:
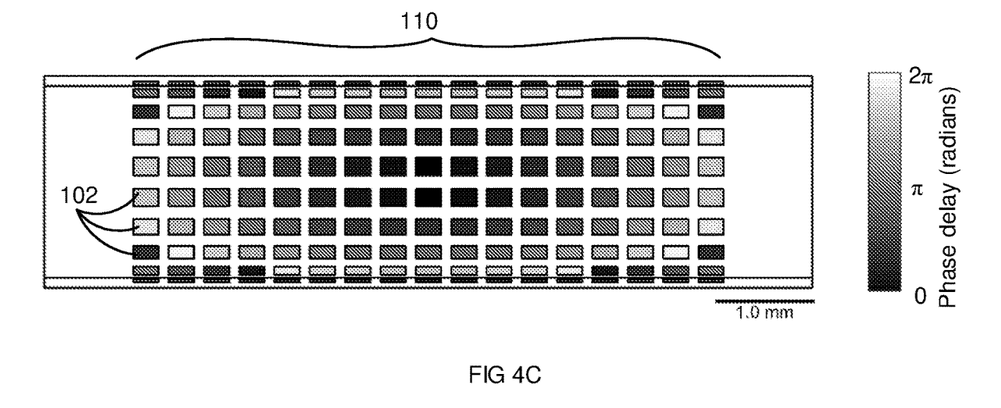
FIG. 4C illustrates phase delay applied to each transducer element for the simulation shown in FIGS. 4A and 4B for the device of FIGS. 1A to 1D.

FIG. 4C is a phase diagram representing the simulated phase delays which, for the device represented in FIGS. 1A to 1D, are applied to each transducer element 102 in the transducer array 110 to focus the emitted ultrasound signals such that the acoustic energy emitted from the transducer array 110 converges on the neuronal target 202. Here, the degree of darkness represents the phase shift which must be applied for each transducer element 102. The shading scale ranges from 0 to 2π since the phase delay for the ultrasound signal emitted from each transducer 102 in the transducer array 110 may be changed by up to 2π radians. Phase delays which exceed 2π may have integer multiples of 2π subtracted, creating an equivalent phase shift within the range 0 to 2π radians. This example demonstrates that it is possible to focus acoustic energy emitted from the transducer array by controlling the phase delay of each transducer element.

Example 2

A simulation of a neural stimulation was executed using k-Wave to demonstrate beam steering around the array. The simulation parameters are shown in Table 1 with the exception of the focal point parameters which were chosen to steer the beam 10 degrees around the array (FIGS. 5A-C and FIG. 7).

Figure 5A:
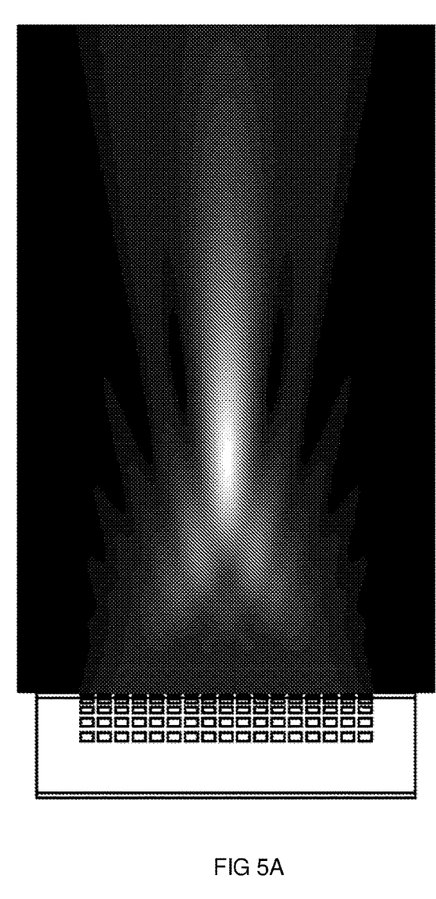
FIGS. 5A and 5B are normalised intensity plots for a simulated endoluminal neurostimulation device showing steering of acoustic energy angularly around the array, deployed in a brain model viewed from the side of the device as represented in FIG. 1D and the end of the device as represented in FIG. 1B respectively.
Figure 5B:
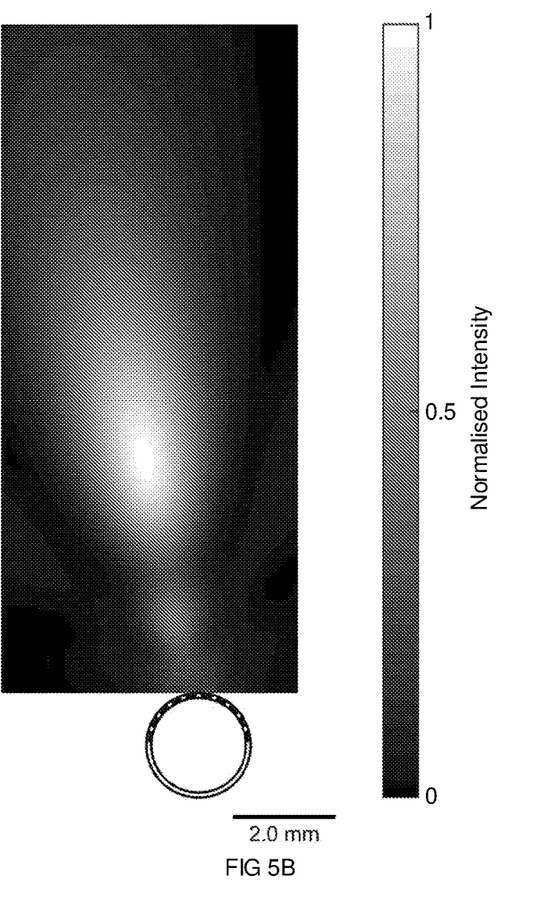
Figure 5C:
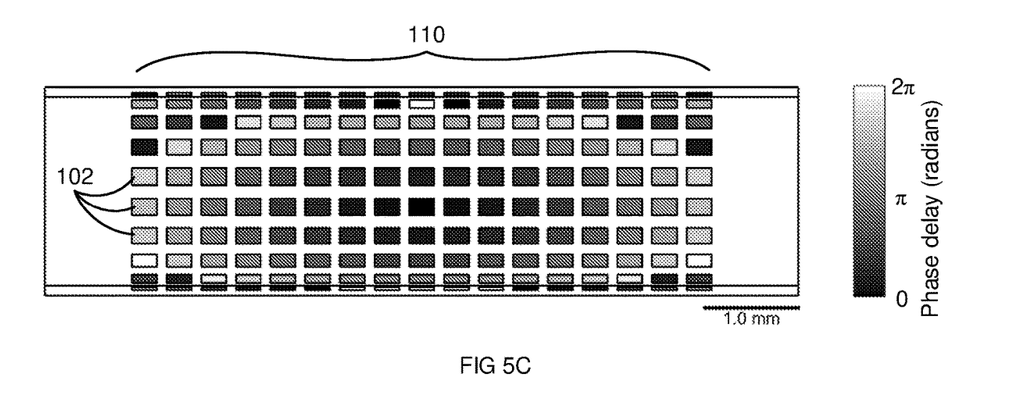
FIG. 5C illustrates phase delay applied to each transducer element for the simulation shown in FIGS. 5A and 5B for the device of FIGS. 1A to 1D.
Figure 7:
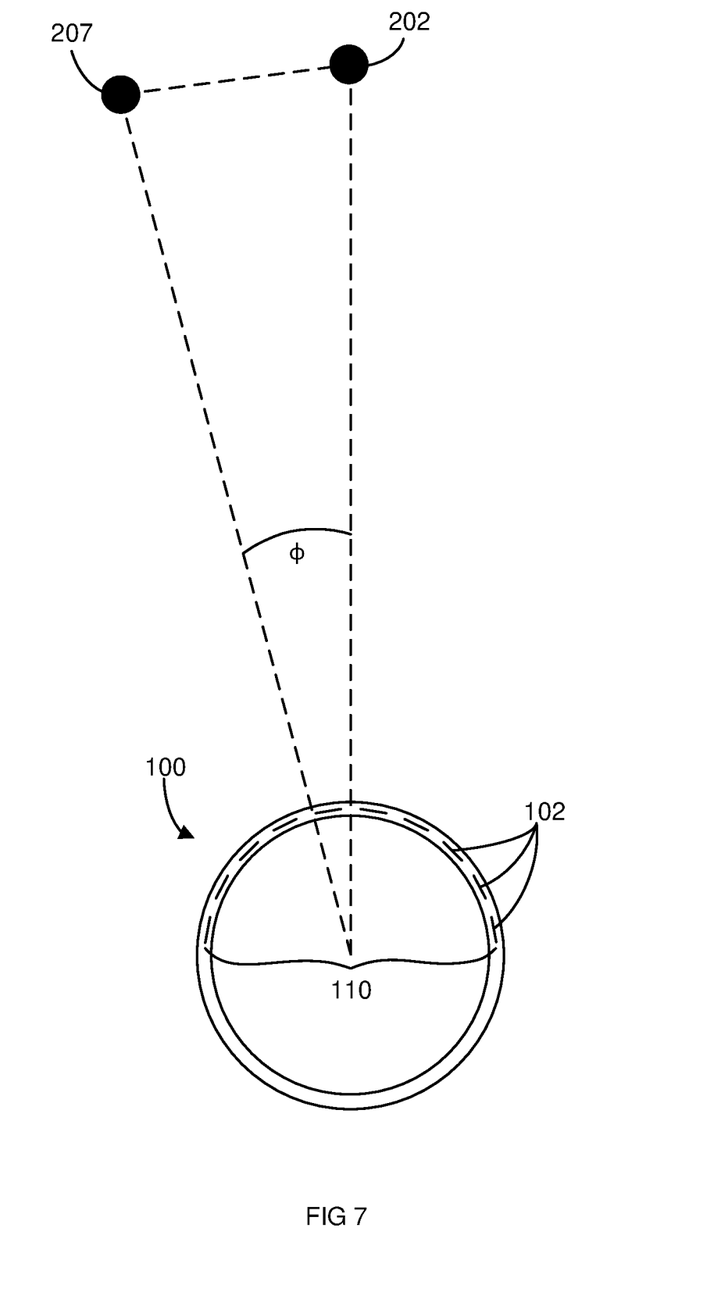
FIG. 7 is a schematic drawing illustrating a neuronal target to which acoustic energy of an endoluminal neurostimulation device is steered angularly around the transducer array.

FIGS. 5A and 5B are normalised intensity plots as viewed from the side of the device in FIG. 1D and the end of the device in FIG. 1B, respectively. FIGS. 5A and 5B show that for the simulated device, the ultrasound signals emitted from the transducer elements 102 are steered such that the acoustic energy emitted by the transducer array 110 is maximised at a neuronal target 207 as represented in FIG. 7, which is located 10 degrees ($\phi$) around transducer array 110 from an initial neuronal target 202. FIG. 5C is a phase diagram representing the simulated phase delays which, for the device represented in FIGS. 1A-D, are applied to each transducer element 102 in the transducer array 110 to steer the emitted ultrasound signals such that the acoustic energy transmitted from the transducer array converges on the neuronal target 207. This example demonstrates that it is possible to steer the acoustic energy angularly around the array by controlling the phase delay of the transducer elements, without the need to relocate or re-orient the device in the lumen.

Example 3

A further simulation of a neural stimulation was executed using k-Wave to demonstrate beam steering along the array. The simulation parameters are shown in Table 1 with the exception of the focal point parameters which were chosen to steer the beam 1 mm along the longitudinal dimension of the array (FIGS. 6A-C and FIG. 3).

Figure 6A:
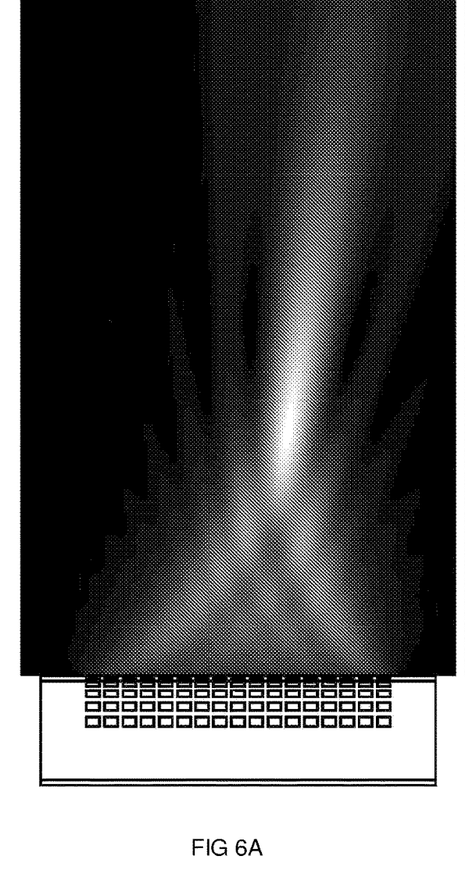
FIGS. 6A and 6B are normalised intensity plots for a simulated endoluminal neurostimulation device showing steering of acoustic energy along a longitudinal dimension of the array, deployed in a brain model viewed from the side of the device as represented in FIG. 1D and the end of the device as represented in FIG. 1B respectively.
Figure 6B:
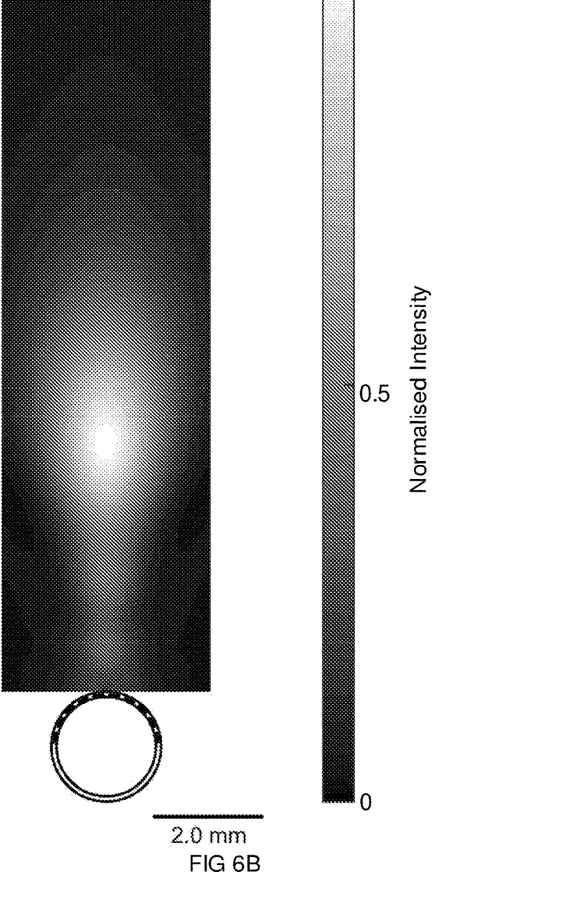
Figure 6C:
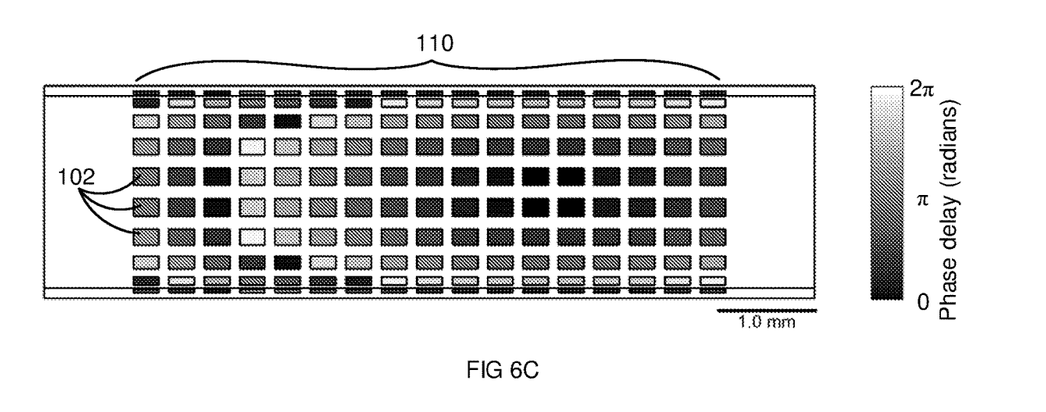
FIG. 6C illustrates phase delay applied to each transducer element for the simulation shown in FIGS. 6A and 6B for the device of FIGS. 1A to 1D.

FIGS. 6A and 6B are normalised intensity plots as viewed from the side of the device in FIG. 1D and the end of the device in FIG. 1 B, respectively. FIGS. 6A and 6B show that for the simulated device, the ultrasound signals emitted from the transducer elements 102 are steered such that the acoustic energy emitted by the transducer array is maximised at a neuronal target 203 as represented in FIG. 3 which is located 1 mm along the transducer array from an initial target 202. FIG. 6C is a phase diagram representing the simulated phase delays which, for the device represented in FIGS. 1A-D, are applied to each transducer element 102 in the transducer array 110 to steer the emitted ultrasound signals such that the acoustic energy transmitted from the transducer array converges on the neuronal target 203. This example demonstrates that it is possible to steer the acoustic energy longitudinally with respect to the array, without the need to relocate or re-orient the device in the lumen.

It is to be understood that while examples demonstrated beam steering around or along the array, the beam may be steered both around and along the array simultaneously.

An implantable endoluminal neurostimulation device according to embodiments of the present disclosure has numerous advantages including that it can modulate neural activity, can emit energy that penetrates deep into tissue, and can be focussed within a small volume. Moreover, open brain surgery is not required for implantation. This leaves open numerous opportunities for clinical application including as an alternative to conventional DBS. Because ultrasound is not subject to current spreading, it may modulate a smaller volume of neurons than with electrical methods providing fewer adverse side effects.

Since the device may be deployed within a blood vessel, a craniotomy is not required for implantation in the brain vasculature to achieve DBS by ultrasound. Instead, catheter angiography and other minimally invasive techniques may be used to deploy the device to the vein. Placing the ultrasound transducers inside the brain and closer to the target tissue, rather than on the exterior of the skull, removes the highly absorbing skull from the beam path and permits higher ultrasound frequencies to be used resulting in superior spatial precision over transcranial focussed ultrasound.

In addition, since ultrasound signals emitted from the transducer elements may be focussed and steered within the nearby tissue, the device may focally modulate a neural population a short distance away from the device. If the device is implanted in a non-optimal position, the beam can be steered to shift the focal point within the tissue thus compensating from the wrongly placed device without needing to re-position the device itself. Modulation of several distant neuronal populations may be achieved by forming an ultrasound beam with multiple focal points, and these may be stimulated simultaneously or sequentially by multiplexing the excitation signals.

Because the present disclosure allows for focussing and/or steering of the acoustic energy emitted from the device, new targets for DBS can be investigated by steering the beam in situ and monitoring the effect of stimulation on different targets in the brain. Thus, in addition to potential deployment sites in the brain to treat Parkinson's disease, other chronic conditions such as epilepsy, obsessive compulsive disorder, addiction and the like may be treated by focussing and steering the energy on one or more neuronal targets under investigation for therapeutic benefit near the device once it has been deployed in the brain vasculature. The present disclosure may also have utility in treating pain and autoimmune disorders by stimulation of the vagal nerve.

Where the terms "comprise", "comprises", "comprised" or "comprising" are used in this specification (including the claims) they are to be interpreted as specifying the presence of the stated features, integers, steps or components, but not precluding the presence of one or more other features, integers, steps or components or group thereof.

It is to be understood that various modifications, additions and/or alterations may be made to the parts previously described without departing from the ambit of the present disclosure as defined in the claims appended hereto.

It is to be understood that the following claims are provided by way of example only, and are not intended to limit the scope of what may be claimed. Features may be added to or omitted from the claims at a later date so as to further define or re-define the invention or inventions.

The invention claimed is:

1. An endoluminal neurostimulation device including:
    a plurality of ultrasound transducer elements forming a transducer array;
    the plurality of transducer elements are arranged in a grid arrangement having at least two dimensions and are provided on or in a substrate layer that is adapted for endoluminal delivery to a deployment site in a lumen of a subject;
    wherein the plurality of transducer elements are operable to focus acoustic energy emitted from the transducer array by controlling one or more of a phase delay and a time delay of ultrasound signals emitted from the plurality of transducer elements such that acoustic energy emitted from the transducer array is maximized at a neuronal target near the deployment site to achieve stimulation thereof, and
    wherein the device is configurable to adopt a delivery configuration in which the substrate layer and the transducer array are receivable in a delivery lumen for endoluminal delivery to the deployment site, and to adopt a deployed configuration in which the substrate layer is arranged with the plurality of transducer elements coupled, directly or indirectly with the luminal wall once deployed from the delivery lumen;
    wherein the substrate layer and the transducer array have a substantially tubular overall shape when deployed in the lumen of the subject; and
    wherein the substrate layer is flexible to accommodate contours within the lumen of the subject in which the device is deployed.

2. The endoluminal neurostimulation device according to claim 1, wherein the plurality of transducer elements are operable to steer the focussed acoustic energy in a plurality of dimensions by controlling one or more of the phase delay and the time delay of ultrasound signals emitted from each of the plurality of transducer elements.

3. The endoluminal neurostimulation device according to claim 1, wherein the substrate layer has one or more of:
    (a) elastic properties such that it is able to be stretched longitudinally to adopt the delivery configuration and reshapes when deployed from the delivery lumen to adopt the deployed configuration when in situ; and
    (b) collapsible or compressible properties such that is able to adopt the delivery configuration and expandable when deployed from the delivery lumen to adopt the deployed configuration when in situ.

4. The endoluminal neurostimulation device according to claim 1, wherein the plurality of transducer elements are arranged on or in the substrate layer to direct ultrasound signals only towards the neuronal target.

5. The endoluminal neurostimulation device according to claim 1, wherein the acoustic energy emitted from the plurality of transducer elements is within a range of 0.5 MHz to 60 MHz, preferably 0.5 MHz to 30 MHz, more preferably 0.5 MHz to 20 MHz and more preferably still, 0.5 MHz to 5 MHz.

6. The endoluminal neurostimulation device according to claim 1, wherein the device includes a control circuit performing one or more of:
    (a) controlling operation of the plurality of transducer elements to achieve one or both of focus and steering of the acoustic energy emitted from the transducer array
    (b) disabling transducer elements in the transducer array that are not required to achieve therapeutic neurostimulation;
    (c) controlling one or both of the amplitude and the frequency of the ultrasound signals emitted by each of the plurality of transducer elements in the transducer array;
    and
    (d) focusing and/or steering the ultrasound signals emitted from the plurality of transducer elements so that the acoustic energy emitted from the transducer array is maximized at a plurality of neuronal targets;
    wherein the control circuit resides:
        i) on or in one or both of the substrate and a backing layer of the transducer array; or ii) in a hermetically sealed housing that is configured for subcutaneous implantation in the subject and operatively coupled with the transducer array by one or more wires.

7. The endoluminal neurostimulation device according to claim 1, including one or both of a backing layer and a matching layer covering at least part of the substrate layer on or in which there are transducer elements.

8. The endoluminal neurostimulation device according to claim 1, wherein the plurality of transducer elements in the grid arrangement are spaced having a pitch of less than half of a wavelength of the ultrasound signals emitted from the transducer elements.

* * * * *